US010456075B2

(12) United States Patent
Auchinleck et al.

(10) Patent No.: US 10,456,075 B2
(45) Date of Patent: Oct. 29, 2019

(54) METHOD FOR CALIBRATING APPARATUS FOR MONITORING REHABILITATION FROM JOINT SURGERY

(71) Applicant: Claris Healthcare Inc., Vancouver (CA)

(72) Inventors: Geof Auchinleck, Vancouver (CA); Paul Sharman, Vancouver (CA)

(73) Assignee: Claris Healthcare Inc., Vancouver (CA)

( * ) Notice: Subject to any disclaimer, the term of this patent is extended or adjusted under 35 U.S.C. 154(b) by 372 days.

(21) Appl. No.: 15/469,641

(22) Filed: Mar. 27, 2017

(65) Prior Publication Data

US 2018/0271432 A1    Sep. 27, 2018

(51) Int. Cl.
*A61B 5/00* (2006.01)
*A61B 5/11* (2006.01)
*A61B 5/107* (2006.01)

(52) U.S. Cl.
CPC .......... *A61B 5/4528* (2013.01); *A61B 5/1071* (2013.01); *A61B 5/11* (2013.01); *A61B 5/4833* (2013.01); *A61B 5/002* (2013.01); *A61B 2505/09* (2013.01); *A61B 2560/0223* (2013.01); *A61B 2562/0219* (2013.01)

(58) Field of Classification Search
CPC ....... A61B 5/11; A61B 5/1071; A61B 5/4585; A61B 5/4528; A61B 5/4833; A61B 5/1118; A61B 5/7278
See application file for complete search history.

(56) References Cited

U.S. PATENT DOCUMENTS

| | | | |
|---|---|---|---|
| 8,909,500 B2* | 12/2014 | Heijkants | A61B 5/1071 702/151 |
| 9,597,015 B2* | 3/2017 | McNames | A61B 5/1071 |
| 9,681,826 B2* | 6/2017 | Dunias | A61B 5/1071 |
| 2012/0191147 A1 | 7/2012 | Rao et al. | |
| 2012/0259649 A1 | 10/2012 | Mallon et al. | |
| 2014/0172442 A1 | 6/2014 | Broderick et al. | |
| 2015/0073814 A1 | 3/2015 | Linebaugh et al. | |
| 2015/0045700 A1 | 12/2015 | Cavanagh et al. | |
| 2016/0310066 A1 | 10/2016 | Wiedenhoefer et al. | |

OTHER PUBLICATIONS

Extended European Search Report issued by the European Patent Office dated Nov. 24, 2017 in European Patent Application No. 17177831.9-1952, which is assigned to the assignee of the present application.
U.S. Appl. No. 15/070,341, Apparatus and Method for Monitoring Rehabilitation from Joint Surgery, filed Mar. 15, 2016 and having the same applicant as the present application.

(Continued)

*Primary Examiner* — Max F Hindenburg
(74) *Attorney, Agent, or Firm* — Hancock Hughey LLP (57) ABSTRACT

A method for calibrating sensors applied to a patient to monitor rehabilitation is disclosed. The calibration method according to the invention that is insensitive to changes in the patient's body position during the calibration procedure—calibration of the flex sensors is facilitated regardless of what orientation they may be applied to the thigh and shank of patient. The calibration method uses three-axis accelerometers defined by software incorporated in local computer.

15 Claims, 9 Drawing Sheets

(56) References Cited

OTHER PUBLICATIONS

Alonge, Francesco et al., The Use of Accelerometers and Gyroscopes to Estimate Hip and Knee Angles on Gait Analysis, Sensors, 14, 8430-8446, 2014.
Tognetti, Alessandro et al., Wearable Goniometer and Accelerometer Sensory Fusion for Knee Joint Angle Measurement in Daily Life, Sensors, 15, 28435-28255, 2015.
Caroselli, Alessio et al., Quasi-Real Time Estimation of Angular Kinematics Using Single-Axis Accelerometers, Sensors, 13, 918-937, 2013.
Dini, Velentina et al., Correlation Between Wound Temperature Obtained With an Infrared Camera and Clinical Wound Bed Score in Venous Leg Ulcers, Wounds, vol. 27—Issue 10—Oct. 2015.
Dae-Hyeong, Kim et al., Abstract: Thin, Flexible Sensors and Actuators as 'Instrumented' Surgical Sutures for Targeted Wound Monitoring and Therapy, Small, vol. 8, Issue 21, Nov. 5, 3023, pp. 3263-3268, Aug. 14, 2012.
Fornano, Carlo Luca et al., Healing of surgical site after total hip and knee replacements show similar telethermographic patterns, Journal Orthopaed Traumatol (2011) 12:81-86, May 5, 2011.
U.S. Appl. No. 15/070,341, filed Mar. 15, 2016, and which is assigned to the same assignee as this application.
U.S. Appl. No. 15/103,259, filed Jun. 27, 2016, and which is assigned to the same assignee as this application.

* cited by examiner

METHOD FOR CALIBRATING APPARATUS FOR MONITORING REHABILITATION FROM JOINT SURGERY

FIELD OF THE INVENTION

The present invention relates to apparatus and methods for monitoring the compliance of a patient to the rehabilitation regimen that is prescribed for preparation for and recovery from joint surgery such as total joint arthroplasty. More specifically, the present invention relates to the use of sensors applied to a post-surgical patient for the purpose of detecting, acquiring and measuring the patient's body position, movement and temperature and for using acquired data for tracking the patient's progress during rehabilitation, and to methods for calibrating the sensors.

Joint arthroplasty is a surgical procedure for resurfacing or replacing those parts of knee, hip, elbow, shoulder and other joints that are damaged, typically from arthritis, in older adults. Knee arthroplasty is a very common procedure—more than 720,000 were done in the United States in 2015—and is rapidly increasing as a result of an aging population.

A key factor in the success of a joint arthroplasty is the compliance of the patient with the required rehabilitation regimen. This regimen may begin prior to surgery—certain exercises and stretches are sometimes prescribed in advance of surgery to improve the chances of success—and is certainly required for some months after the surgery is complete. Rehabilitation may include such activities as flexing the affected joint through a certain range of motion, applying ice or heat to the joint, spending appropriate amounts of time standing and walking, reporting joint pain and monitoring the surgical site for signs of infection or drainage.

Rehabilitation is usually managed by a physiotherapist or other medical professional who instructs the patient in a clinical setting, then checks with the patient occasionally to monitor their progress. This means that the patient is expected to be self-motivated to follow the required regimen and accurately report to the caregiver their level of compliance. Many find this difficult to do and may not be entirely honest about their level of compliance.

To encourage better compliance, it would be advantageous to provide a patient with timely feedback and encouragement as to their progress, and to provide quantitative measurements as to their progress, both to the patient and their caregivers.

Three kinds of measurements can provide information of value. The first is measurement of the number of flexions, degree of flexion and maximum and minimum amount of flexion of the affected joint; the second is measurement of the temperature near the surgical site; and the third is the position of the patient's body. The number and the degree of flexions including the maximum and minimum flex angles is indicative of the patient's activity level and progress towards re-establishing a full range of motion. The temperature near the wound site can provide measure of how often and for how long the patient applies ice to their joint. The position of the patient's body (sitting, standing, lying down), combined with the joint flexion information allows detection of the duration of standing, walking and resting of the joint.

Using electronic sensors to measure joint flexion has been demonstrated in the laboratory. Several published papers show the use of integrated circuit accelerometers or capacitive, resistive or inductive flex sensors to detect joint movements and range of motion. Similarly, there are many well-known ways to measure temperature using electronic and mechanical thermometers. Body position can be determined by attaching an accelerometer to the patient's thigh and/or shin to detect the direction of gravitational acceleration.

Existing devices for measuring joint motion, body orientation and temperature require separate sensors connected to a computer for collecting data for interpretation by a caregiver. These systems do not provide a convenient single unit for measuring the required parameters, nor do they provide for storage of the data for later transmission to a caregiver's computer. In addition, a single temperature sensor near the wound site may provide misleading data if the patient moves into a hot or cold environment, as there is no way, with one sensor, to tell if the temperature increase or decrease is a local effect (caused by infection or icing of the joint).

The prior art also fails to teach the combination of data from motion, position and temperature sensors into a patient coaching system and caregiver management system. Such a system can be used by a caregiver to set specific goals (such as number of repetitions of joint flexion, target ranges of motion or target temperature and duration during icing, or maximum and minimum periods of time walking or standing) and to provide the patient with feedback and encouragement as to achievement of those goals based on measurements by the sensors.

SUMMARY OF THE INVENTION

The current invention describes apparatus and method for setting rehabilitation goals for a patient, measuring their movements, storing the movement data for later transfer to a computer, displaying progress indicators and inspirational messages based on progress towards goals, reporting movement, body orientation and temperature data to a caregiver so that they monitor compliance with the prescribed recovery regimen.

One advantage of the current invention is the use of two temperature sensors to monitor patient skin temperature—one located on the skin near the surgical wound site and another on the skin some distance from the wound site, so that the wound site temperature can be compared to a basal skin temperature, eliminating environmental variations that might effect the temperature measurements.

In another aspect, the sensor apparatus in accordance with the current invention provides for data storages and wireless communications between the sensor apparatus and a computer or computer network, such that readings made by the sensors can be stored within the sensor apparatus, then transmitted wirelessly to a computer or network whenever a wireless connection is available, therefore eliminating the need for the patient to remain within wireless communications range of a computer, without risking loss of measurement data.

In a further aspect, the sensor apparatus in accordance with the invention incorporates means for easy attachment and removal from a patient's limb while maintaining the position and orientation of the sensor, in order to allow the patient to remove the sensor while bathing or sleeping, yet return the sensor to a known location and orientation, eliminating the need for frequent re-calibration. A further refinement uses a magnetic switch in the sensor electronics to enable reducing the power consumption of the sensor when it is removed from the patient's leg.

The current invention also teaches a method for calibrating a sensor according to the invention that is insensitive to changes in the patient's body position during the calibration procedure.

BRIEF DESCRIPTION OF THE DRAWINGS

These and other objects, features and advantages of the present invention will become apparent upon reference to the following detailed description of the exemplary embodiment presented herein and to the drawings wherein.

DETAILED DESCRIPTION OF THE INVENTION AND ILLUSTRATED EMBODIMENTS

Figure 1:
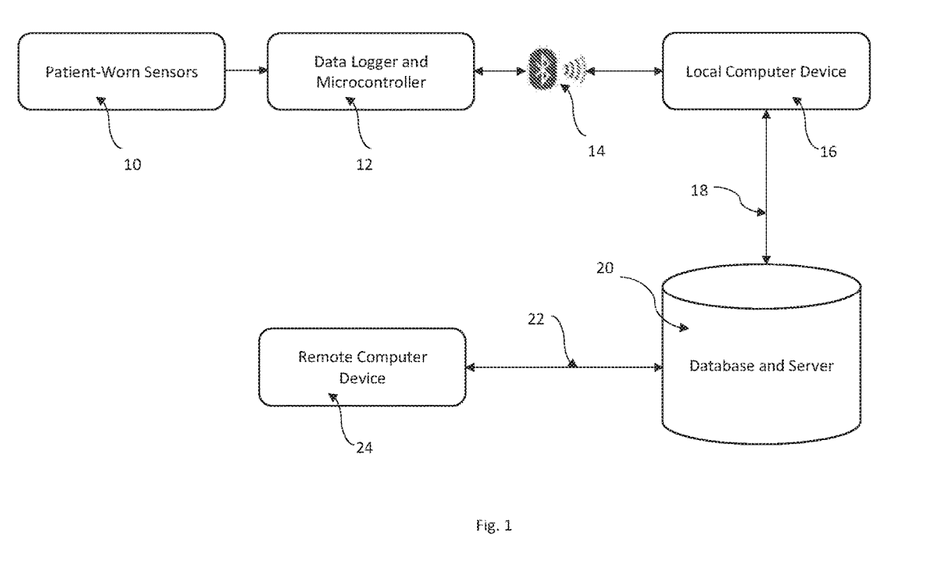
FIG. 1 is a block diagram of an apparatus according to the invention.

FIG. 1 illustrates the major functional components of the preferred embodiment according to the invention. Patient-worn sensors 10 are connected to data logger and microcontroller 12, both of which are described more fully hereinafter, such that the microcontroller can cause data to be read from sensors 10 and stored in memory. At pre-determined intervals, microcontroller 12 tests to see if a connection to local computer 16 can be made through wireless data connection 14, which in the preferred embodiment is a Bluetooth connection, but may be a WiFi or other data connection. If a connection is available, microcontroller 12 retrieves data from sensors 10 from the memory and sends it across wireless data connection 14 to local computer 16. Local computer 16, which in the preferred embodiment is an Android tablet computer such as a Samsung Galaxy Tab (Samsung Corporation), then transfers the data, using Internet connection 18, to database and server 20, which, in the preferred embodiment is a 'cloud service' such as those provided by Heroku and Amazon.

Also connected to database and server 20 is remote computer 24, via Internet connection 22, which may be any computer capable of running a web browser such as Google Chrome or the like. Thus, it can be seen that through the various devices and connections described, data from sensors 10 can be delivered to database and server 20, from where it can be retrieved by remote computer 24 for viewing and interpretation by a user of remote computer 24.

Note that Internet connections 18 and 22 permit communications in the opposite direction to that described—remote computer 24 can send information via Internet connection 22 to database and server 20, from whence it can be further sent to local computer 16. In this way it is possible for remote computer 24 to cause computer 16 to display messages, images, videos or other information on local computer 16.

Figure 2:
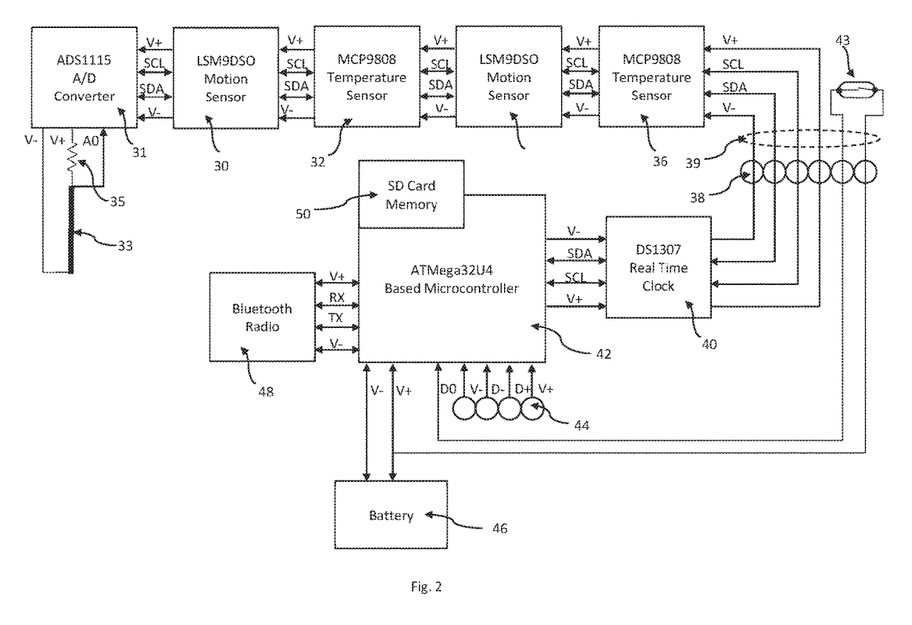
FIG. 2 is a schematic representation of the sensor and data logger components of the apparatus shown in FIG. 1.

FIG. 2 more fully illustrates patient worn sensors 10 and data logger and microcontroller 12. In the preferred embodiment, data logger and microcontroller 12 is made up of ATMega32U4 processor board 42, connected to SD card memory unit 50, which in the preferred embodiment is an Adafruit Feather 32u4 Adalogger (Adafruit Industries LLC, NY, N.Y.). Incorporated into processor board 42 is USB connector 44, serial communications connections, I2C bus connections and battery charging circuitry. Battery 46 is a lithium polymer 3.7 volt 12 mAh battery, which in the preferred embodiment is a PKCell LP503562, which is connected to the battery pins of processor board 42.

Magnetic switch 43, which in the preferred embodiment is a Littlefuse MDSM-4R normally open type reed switch which closes in the presence of a magnetic field, is connected between the positive lead of battery 46 and digital input D0 of microprocessor 42, allowing the state of magnetic switch 43 to be read by the software running on microprocessor 42. This permits placing microprocessor 42 into a low power consumption mode when it is not in proximity to a magnet, thereby reducing drain on battery 46.

Bluetooth radio 48 is embodied with an Adafruit BlueFruit EZ Link module. This module is connected to the auxiliary power supply connections of processor board 42 and to the serial data transmit (TX) and receive (RX) pins of processor board 42.

The remaining modules of data logger and microcontroller 12 and patient worn sensors 10 are connected to processor board 42 using the industry standard I2C bus. This communications bus provides electrical power and digital communications to 100 or more modules connected on the same set of four wires. As each device connected to the I2C bus has a unique digital address, the software running on microcontroller 12 can request and receive data from each module as required.

Real time clock 40 is an I2C module based on the DS1307 real time clock chip. In the preferred embodiment, this is an Adafruit DS1307 Real Time Clock module, which includes a battery backup to ensure that real time clock data is preserved even if battery 46 should become exhausted.

Also connected to the I2C bus are two MCP9808 temperature sensors (Adafruit MCP9808) and two LSM9DSO motion sensors (Adafruit LSM9DSO). Motion sensor 30 is connected to the distal end of I2C cable 39 so that it may be attached distal to the patient's affected joint as hereinafter described; temperature sensor 32 is connected to the cable 39 some distance proximal to motion sensor 30, such that it may be attached to the patient's skin near the surgical site; and motion sensor 34 and temperature sensor 36, are connected some distance proximal to temperature sensor 32 so that they can be attached to the skin proximal to the patient's affected joint. As detailed below, temperature sensor 32 is attached to the patient near enough to the surgical site that the sensor is capable of measuring increases (or decreases)

in temperature at the surgical site, which could be indicative of infection (or icing). Temperature sensor 36 is attached to the patient spaced away from sensor 32 by enough distance that the sensor 36 measures a basal skin temperature that is not effected by an increase or decrease in temperature at the surgical site where the sensor 32 is located.

Cable 39 connecting real time clock 40 and temperature sensor 36 includes connector 38, which allows the temperatures sensors 32 and 36 and motion sensors 30 and 34 to be disconnected from real time clock 40, thus making the module containing real time clock 40, processor board 42, Bluetooth radio 48, SD card memory 50 and battery 46 separable from the sensor components.

Figure 3:
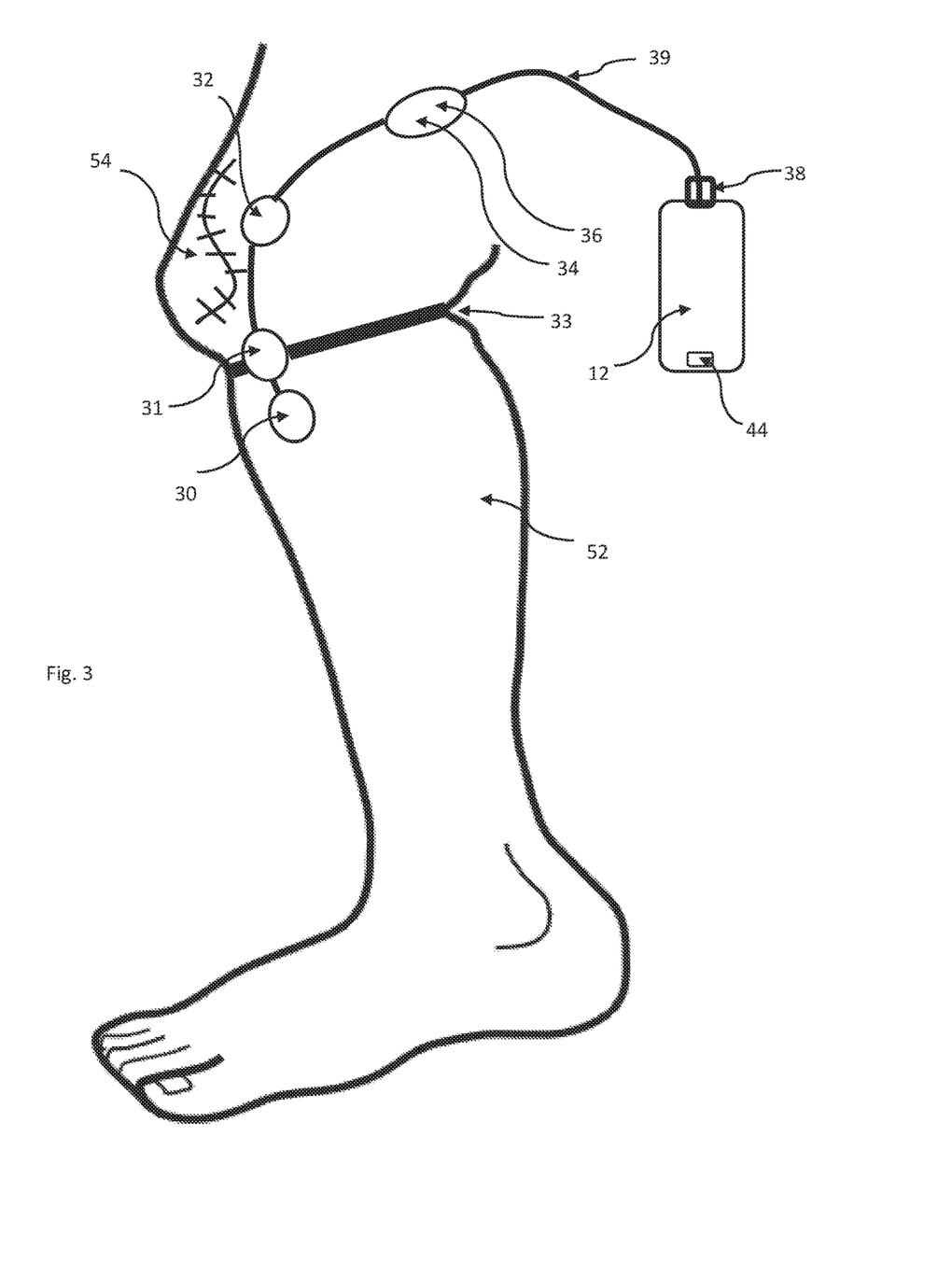
FIG. 3 is a schematic illustration of a post-operative patient's leg illustrating how the sensors, data logger and microcontroller may be applied to the patient's leg.

FIG. 3 shows how patient worn sensors 10 and data logger and microcontroller 12 might be applied to the leg of patient 52 during recovery from knee surgery. Motion sensor 30 is applied to the patient's leg below the knee and may be taped in place, attached to the surgical dressing, or tucked inside an elastic bandage applied to the leg. Similarly, temperature sensor 32 is attached to the leg, but is located a near as practicable to surgical incision 54. In the preferred embodiment, temperature sensor 36 and motion sensor 34 are contained within the same enclosure and are attached to the leg of patient 52 above the knee. All of the sensors are connected with cable 39, which is connected to data logger and microcontroller 12 with connector 38. Microcontroller 12 encloses real time clock 40, processor board 42, SD memory 50, Bluetooth radio 48, battery 46 and USB connector 44. USB connector 44 is accessible such that microcontroller 12 can be plugged into a standard USB cable to recharge battery 46 and to upload programs to processor board 42. In use, microcontroller 12 may be strapped to the leg of patient 52 with an elastic strap, clipped on a belt, or placed in a pocket.

Figure 4:
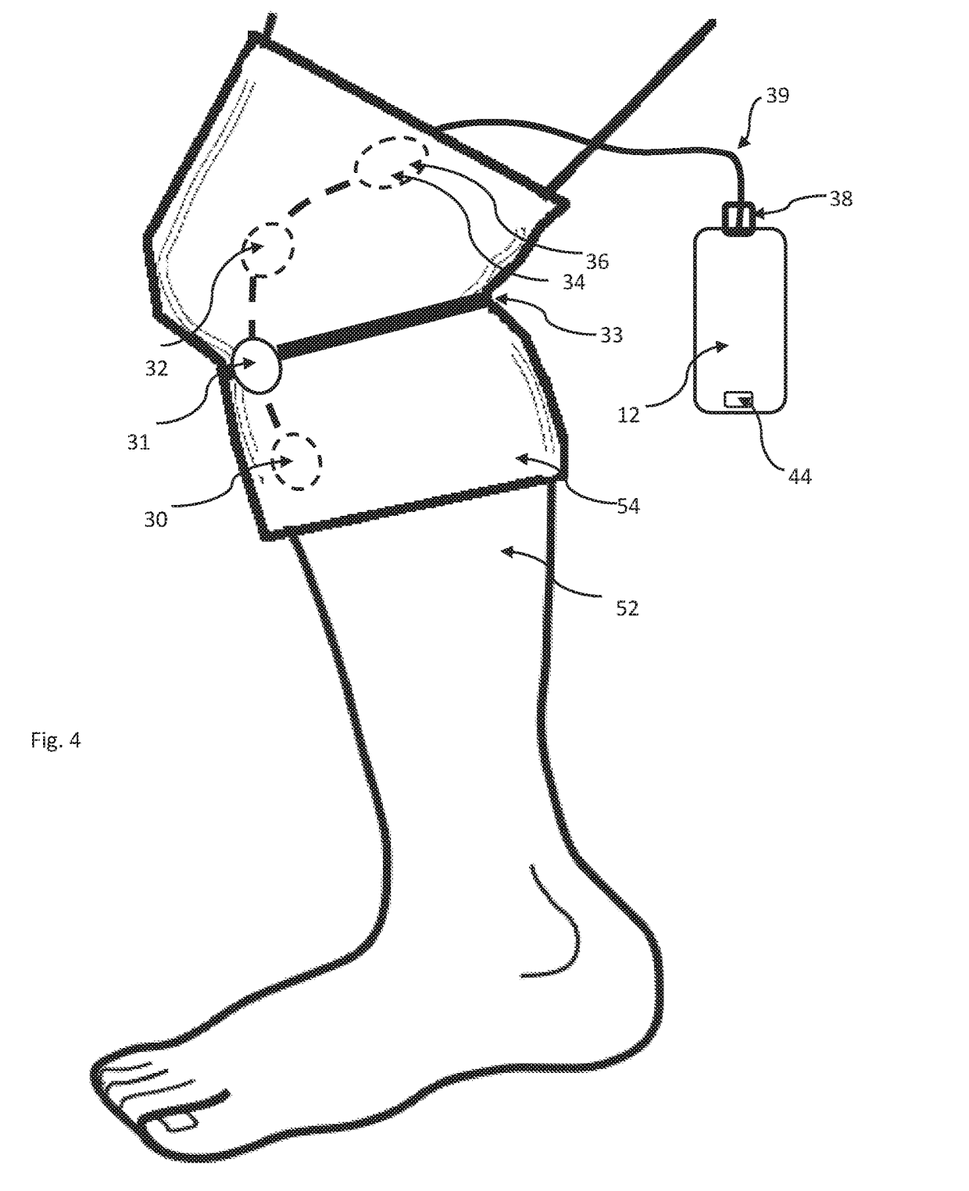
FIG. 4 is a schematic illustration analogous to FIG. 3 except illustrating an alternative embodiment of an apparatus for locating the sensors on the patient's leg.

FIG. 4 shows an alternative means for locating the sensors on a patient's leg in accordance with the invention, as it might be used in rehabilitation from knee surgery. In this embodiment, sensors 30, 32 34 and 36 are fastened inside elastic sleeve 54, all connected via cable 39. The sensors are pre-positioned at locations inside the sleeve such that when the sleeve is pulled up over the knee, the sensors are located in the desired positions. This has the advantage of simplifying the location and attachment of the sensors to the patient.

In typical use, a caregiver uses remote computer 24, to create a record for a new patient using a web application hosted by database and server 20. As part of this setup, the caregiver assigns local computer 16 to patient 52, creating a link between the record for the patient and local computer 16. The caregiver then pairs patient worn sensors 10 to local computer 16 so that data from patient worn sensors 10 is transmitted to local computer 16 using Bluetooth connection 14 from where it is further transferred to database and server 20 over Internet connection 18, where it is stored in a database record associated with patient 52.

As soon as the connection is made, data logger and microcontroller 12 begins to collect data from patient worn sensors 10 and store it locally in SD card memory 50. In the preferred embodiment, data is collected approximately every 1/10 second. From time to time, microcontroller 12 checks to see if there is a connection to local computer 16 available using Bluetooth connection 14. If so, microcontroller 12 transmits any data not previously transmitted to local computer 16. In turn, local computer 16 transmits the data to database and server 20 over Internet connection 18.

From time to time, the caregiver may choose to review the data collected by patient worn sensors 10. Using a web browser on remote computer 24, the caregiver can retrieve data from database and server 20. The web service running on database and server 20 retrieves the data obtained from patient worn sensors 10 and performs an analysis of the data to extract features from the raw data.

Many different techniques for extracting knee joint angles from accelerometer and gyroscope data are known in the art, many of which can be implemented with the sensors 30 and 34 herein described. For example, a first approximation of the knee joint angle can be determined using only the three-axis accelerometers of sensors 30 and 34. In this implementation, the acceleration due to gravity is detected by each sensor to provide an X, Y and Z acceleration measurement that varies depending on the orientation of the sensor with respect to the ground. As sensor 30 is attached to the shank of patient 52 and sensor 34 is connected to the thigh of patient 52, the X, Y and Z axis readings from each sensor define a vector V that represents the orientation of the sensor on the shank or thigh, and the angle between the two resulting vectors represents the angle between the shank and thigh. The formula for determining the angle between two vectors V1 and V2 is:

$$\theta = \cos^{-1}(V1 \cdot V2)/(|V1| \times |V2|)$$

Where • indicates the dot product of the vectors and |V| indicates the magnitude of the vector.

Measuring only accelerations will give a reasonably accurate representation of knee flexion angle when patient 52 is at rest, but will be less accurate when there is any motion. To improve the estimate of the actual knee angle, there are several different filtering techniques to remove signal noise and accelerations due to motions of the patient. A particularly good technique is to use the three axis gyroscopes incorporated in sensors 30 and 34 to detect the angular rotation rate of the shank and thigh of patient 52 when they are moving and use this data to correct the readings taken from the accelerometers. In the preferred embodiment, a Kalman filter is used to make this correction.

The Kalman filter is an algorithm which uses a time series of measurements to estimate the next expected state of the system based on the current and previous states. It produces a statistically optimal estimate of the actual state of the system based on the measurements, even when the measurements include noise. In the case of an accelerometer and gyroscope, the accelerometer will include noise components as a result of motion, while the gyroscope will drift over time. In short, the accelerometer will give a good indication of the direction of gravity (hence the angle of the limb in question) over a long period of time, while the gyroscope will give a good indication of a change in angle over a short period of time, but will become increasingly inaccurate over longer periods of time due to drift. The Kalman filter thus uses both measurements to arrive at a good estimate of the actual orientation of the sensors.

In the preferred embodiment, readings are taken from sensors 30 and 34 every 1/10 of a second. The three acceleration measurements (X,Y and Z axes) and three gyroscope rate measurements (X,Y and Z axes) from sensor 30 are passed through the Kalman filter calculation to arrive at an estimate of the current X, Y and Z angles of sensor 30, which provides a vector representing the orientation of sensor 30 with respect to gravity. Similarly, the three acceleration measurements and three gyroscope rate measurements from sensor 34 are passed through the Kalman filter calculation to arrive at an estimate of the current X, Y and Z angles of sensor 34 with respect to gravity. As described above, the angle between the two resulting vectors is easily calculated.

The mathematics of a Kalman filter are well known in the art. In the preferred embodiment, the Kalman filter calculation is reduced to the following:

$$\text{Rate} = \text{NewRate} - \text{Bias} \quad (1)$$

Where temporary value Rate is calculated as the latest gyroscope rate reading (NewRate) minus the most recently calculated Bias amount. Bias is initially set to 0 and is updated during each pass through the Kalman filter.

$$\text{Angle} = \text{Angle} + \text{DeltaT} \times \text{Rate} \quad (2)$$

Where temporary value Angle is the previous value of Angle plus the time interval since the last reading (DeltaT) times the new Rate calculated in step 1.

$$P[0][0] = P[0][0] + \text{DeltaT} \times (\text{DeltaT} \times P[1][1] - P[0][1] - P[1][0])$$

$$+ Q\_\text{angle}$$

$$P[0][1] = P[0][1] - \text{DeltaT} \times P[1][1]$$

$$P[1][0] = P[1][0] - \text{DeltaT} \times P[1][1]$$

$$P[1][1] = P[1][1] + \text{DeltaT} \times Q\_\text{bias} \quad (3)$$

Where P[ ][ ] is the covariance matrix, Q_angle and Q_bias are constants. This step updates the estimation error covariance.

$$K[0] = P[0][0]/(P[0][0] + R\_\text{Measure}) \quad (4)$$

$$K[1] = P[1][0]/(P[0][0] + R\_\text{Measure})$$

Where constant R_Measure is used to update the Kalman gain matrix K.

$$\text{tempAngle} = \text{newAngle} - \text{Angle} \quad (5)$$

$$\text{Angle} = \text{Angle} + K[0] \times \text{tempAngle} \quad (6)$$

$$\text{Bias} = \text{Bias} + K[1] \times \text{tempAngle} \quad (7)$$

In these steps, the angle calculated during that previous pass through the Kalman filer is subtracted from the new reading of the angle from the accelerometer, newAngle to get tempAngle, the change in angle. This is adjusted by the Kalman gain K[0] calculated in the previous step to arrive at a new value of the estimated actual angle, Angle. Similarly, a new value for Bias is calculated by multiplying the Kalman gain K[1] by tempAngle.

$$P[0][0] = P[0][0] - K[0] \times P[0][0] \quad (8)$$

$$P[0][1] = P[0][1] - K[0] \times P[0][1]$$

$$P[1][0] = P[1][0] - K[1] \times P[1][0]$$

$$P[1][1] = P[1][1] - K[1] \times P[1][1]$$

As a final step of the Kalman filter, the values of the covariance matrix are updated based on the updated Kalman gain.

It can been seen from the above that each of the X, Y and Z axis measurements of the inertial sensor (newAngle) can be combined with the X, Y and Z axis measurements of the gyroscope (NewRate) to arrive at a best estimate of the actual magnitude of gravitational acceleration measured by the sensors with respect to each axis. Doing this for the data read from both of sensors 30 and 34 results in the two vectors from which the angle between the shank and thigh of patient 52 can be calculated, as described above. The data comprises the number of flexions, the degree of flexion and the maximum and minimum amount of flexion of the affected joint. The maximum and minimum flex angle achieved during each flex is important for the assessment of the patient's rehabilitation because it is important to get the joint fully straight as part of the recovery process.

It should be further noted that the vectors of the gravitational acceleration as measured by sensors 30 and 34 can be used to determine the current position of the patient's body. For example, if the gravitational vectors for sensors 30 and 34 are in line with the thigh and shank, patient 52 is standing; if the gravitational vector sensed by sensor 34 is perpendicular to the thigh while the gravitational vector sensed by sensor 30 is in line with the shank, patient 52 is sitting, while if sensors 30 and 34 detect a gravitational vectors perpendicular to the thigh and shank, patient 52 is lying down.

This angle and temperature information read from the sensors may be presented to the caregiver in many different forms, one of which is graphically, as hereinafter described.

Data from the two temperature sensors is also processed by database and server 20 to calculate the difference in temperature measured by temperature sensor 36 and temperature sensor 32. This difference in temperature is meaningful to the caregiver in that an elevation of the temperature measured by temperature sensor 32, which is located near surgical incision 54, with respect to the basal temperature measured by temperature sensor 36, which is located separated from the surgical incision 54 by a great enough distance that the sensor 36 will not detect an elevated temperature at the incision, may be indicative of infection of surgical incision 54. Alternatively, a decrease in the temperature measured by temperature sensor 32 with respect to the basal temperature measured by temperature sensor 36 is a good indication that the patient is applying ice to the surgical site, which is a desirable part of the rehabilitation protocol.

The absolute temperature measured by sensors 32 and 36 is also of clinical interest. A rise in basal temperature as measured by temperature sensor 36, which is removed a distance from surgical incision 54, could indicate body heating due to exercise in the case of a small temperature rise, or a system infection causing a fever in patient 52. Similarly, a fall in the absolute temperature of sensor 32 is likely indicative of icing of the knee joint. Therefore, although there are advantages to considering the temperature differences between sensors 32 and 36, either sensor can provide useful information by itself.

The duration of temperature measured by sensor 32 is of clinical value as well and is data that is collected and analyzed by the present invention. As an example, if the absolute temperature measured by sensor 32 is indicative of the patient icing the joint, then determining the time that the temperature is indicative of icing allows the caregiver to know how long the patient is icing the joint.

Figure 5:
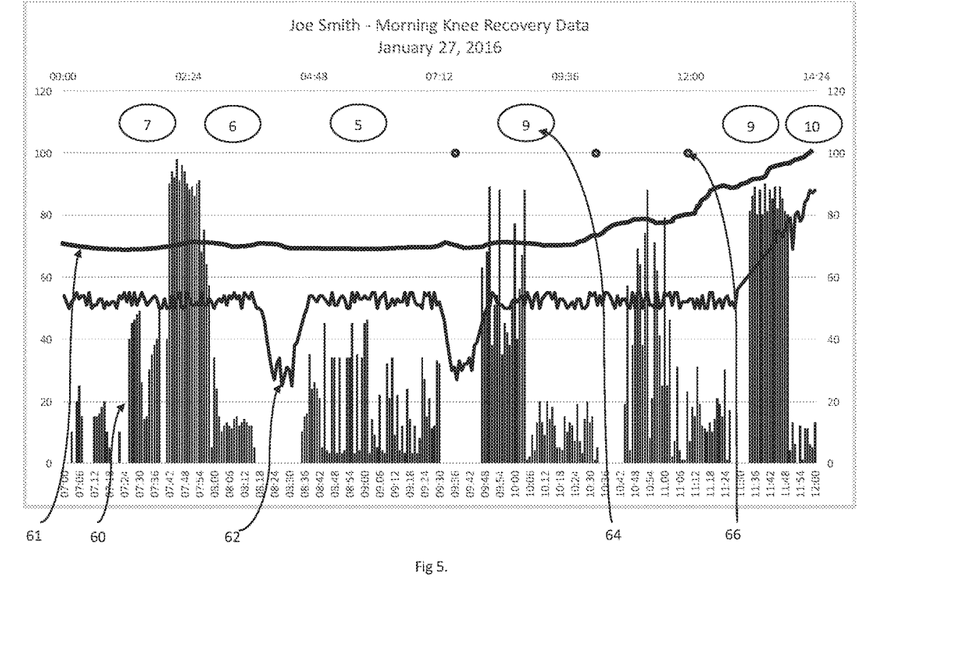
FIG. 5 is a graphical display of how data obtained from patient-worn sensors according the present invention may be displayed on, for example, a computer monitor.

FIG. 5 shows one of many possible ways to display the data obtained from patient worn sensors 10 as processed by database and server 20. In this graphical representation, vertical lines 60 indicate a knee flexion. The height of the line is proportional to the degree of flexion as indicated on the vertical axis. Thus a caregiver can easily determine the degree of activity, number of times the patient has flexed their knee and by what amount.

Line 62 shows the temperature difference between temperature sensors 32 and 36. In the figure, two periods of decreased temperature would indicate to the caregiver that the patient is properly icing their knee. To the right end of the temperature curve, there is a sharp and steady rise in the temperature difference. This would indicate to the caregiver the onset of infection. In this embodiment, the temperature differential is shown, however it is clear that similarly useful information can be conveyed by showing the absolute temperature measured by either or both sensors and the duration of time either or both of the sensors 32 and 36 remain at a given temperature or temperature range.

As the connection between remote computer 24 is connected to local computer 16 via Internet connections 22 and 18 is bi-directional, it is possible for the caregiver to interact with patient 52 using email, text messaging, or video chat using any number of easily available Internet communications tools. In the preferred embodiment, this communications was facilitated using the Claris Companion Android app from Claris Healthcare Inc. (www.clariscompanion.com). The Claris Companion app was integrated with the database and server of the preferred embodiment to add additional useful information to the graphical display of data for the caregiver, as well as to provide additional useful functions. For example, the Claris Companion app is configured to allow patient 52 to voluntarily provide a "pain score" from 1-10, where 1 is no pain at all and 10 is excruciating. Pain scores 64 are displayed along the time axis in FIG. 5 so that the caregiver can correlate the pain score with activity or temperatures. In addition, the Claris Companion app is configured to report whenever the patient chooses to take pain medication, as indicated by marks 66 in FIG. 5.

In addition to the manual communication between the caregiver and patient 52 made possible by the present invention, the preferred embodiment provides automated coaching and encouragement to patient 52 via local computer 16. For example, the caregiver can set goals for patient 52 such as completing 25 repetitions of a knee flex beyond 80 degrees. When database and server 20 calculates that the target repetitions are completed by analyzing the data from patient worn sensors 10, it causes local computer 16 to display a congratulatory message. Similarly, analysis of the temperature data from patient worn sensors 10 can cause local computer 16 to show a confirmation message when patient 52 successfully lowers the temperature of surgical incision 54 by a desired amount, and can then start an on-screen timer to indicate how long the lowered temperature should be maintained. Further automated or manual coaching and encouragement can be provided in the form of instructional videos or photographs, encouraging messages, social interaction with similar patients, and 'gamification' in the form of goals, rewards and progress reporting.

Figure 6:
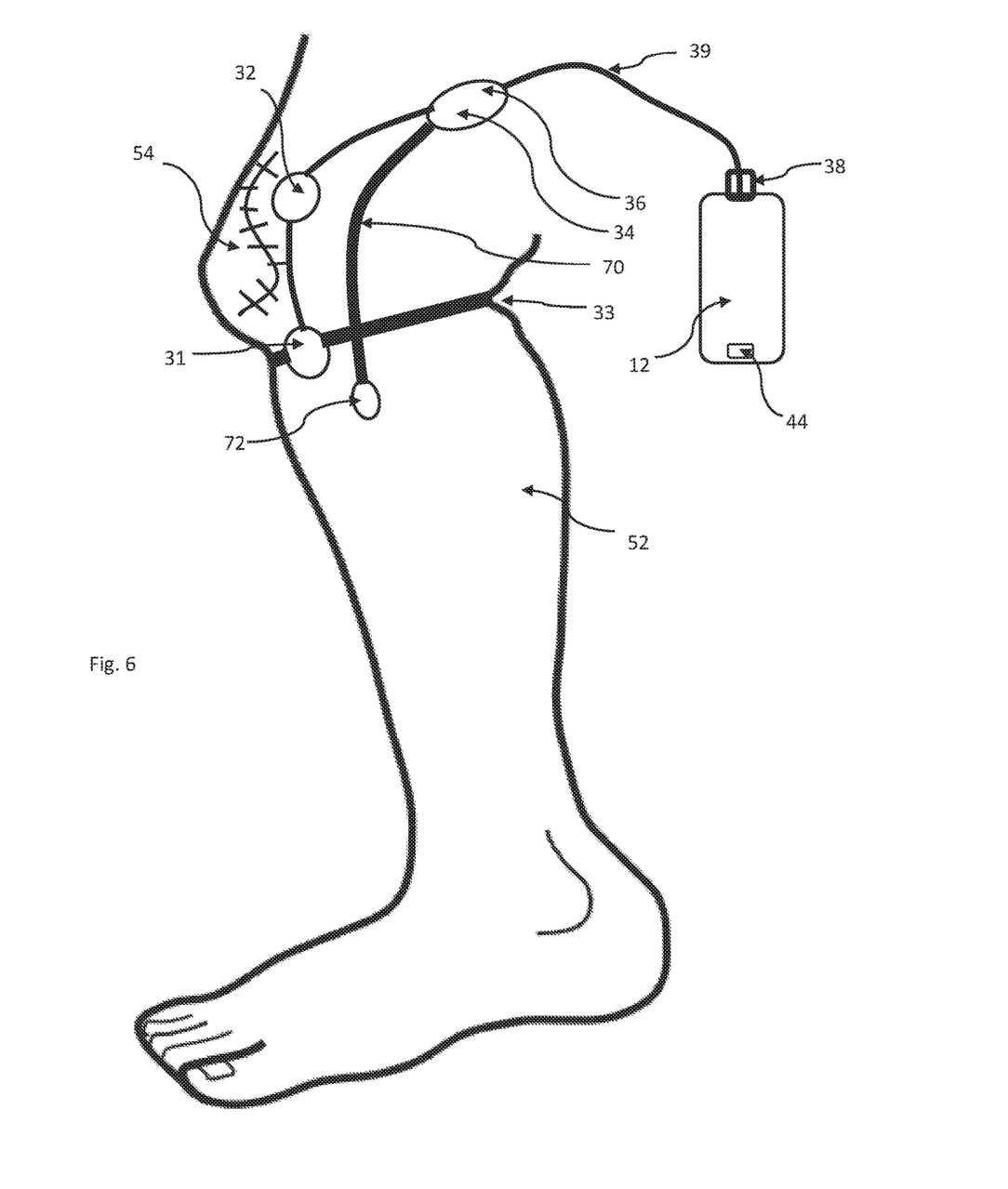
FIG. 6 is a schematic illustration analogous to FIG. 3, except illustrating an alternative embodiment of an apparatus for measuring the flexion of the patient's leg.

FIG. 6 illustrates an alternative sensing means for determining the degree of flexion of the knee of patient 52. In this embodiment, distal motion sensor 30 is replaced with capacitive flex sensor 70, which in the preferred embodiment is a Soft Silicon Bend Sensor (bendlabs.com) that provides a signal proportional to the angle of flexion of sensor 70. Flex sensor 70 is an elongate strip attached to the leg of patient 52 so that the strip extends above, over and below the knee joint using anchor 72 and the case that encloses sensors 36 and 34. As sensor 70 provides a signal directly proportional to the degree of flexion of the knee of patient 52, there is no need to perform mathematical calculations to determine the flexion angle. Although no longer used in the calculation of the flexion angle, motion sensor 34 is retained in order to allow the orientation of the thigh of patient 52 to be measured. Knowing this orientation allows a caregiver to determine the body position of patient 52 while they are flexing their knee. For example, should motion sensor 34 indicate that the thigh of patient 52 is horizontal while the knee is flexed, it would indicate that patient 52 is performing the exercise while sitting, while if motion sensor 34 indicates that the thigh of patient 52 is vertical, it would indicate that the exercise is being performed while standing. Thus, data corresponding to the orientation of the limb that is proximate to the joint relative to a ground plane (i.e., a horizontal reference plane) is an effective in monitoring rehabilitation therapy. Combining the limb orientation data with the dynamic flex data also allows detection of walking and standing. The duration of walking and standing is also an important factor in rehabilitation regimens.

The objective of physiotherapy is to restore normal function of the knee, which is generally accepted to mean a full extension of −10 degrees (i.e. hyperextension of the leg slightly beyond straight) to 110 degrees (i.e. tightly flexed so that the heel is behind the buttock). For patients who are not able to reach the full 120 degree range of motion, it is important to know the absolute values of their maximum extension and flexion. Regardless of the type of sensors used to determine knee flexion angles, calibration of the measured flex angle is required to determine the actual flex angle of the knee. Although either sensor apparatus described herein will measure the change in angle between the thigh and shank, the sensors may be attached to the leg of patient 52 in an orientation with respect to the thigh and shank that is not exactly known in advance. This means that while relative angles can be measured accurately, there is no way to know the absolute angle without calibration.

Figure 7A:
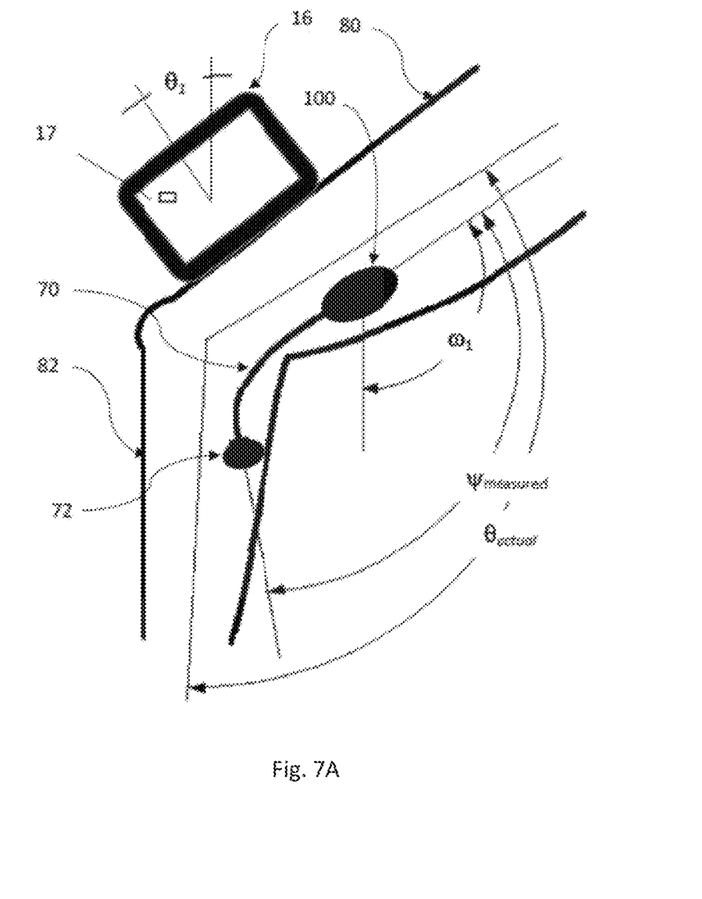
FIG. 7A is an illustration of a calibration procedure that may be followed to calibrate the sensor according to the invention, illustrating a calibration device positioned on the top surface of a patient's thigh.
Figure 7B:
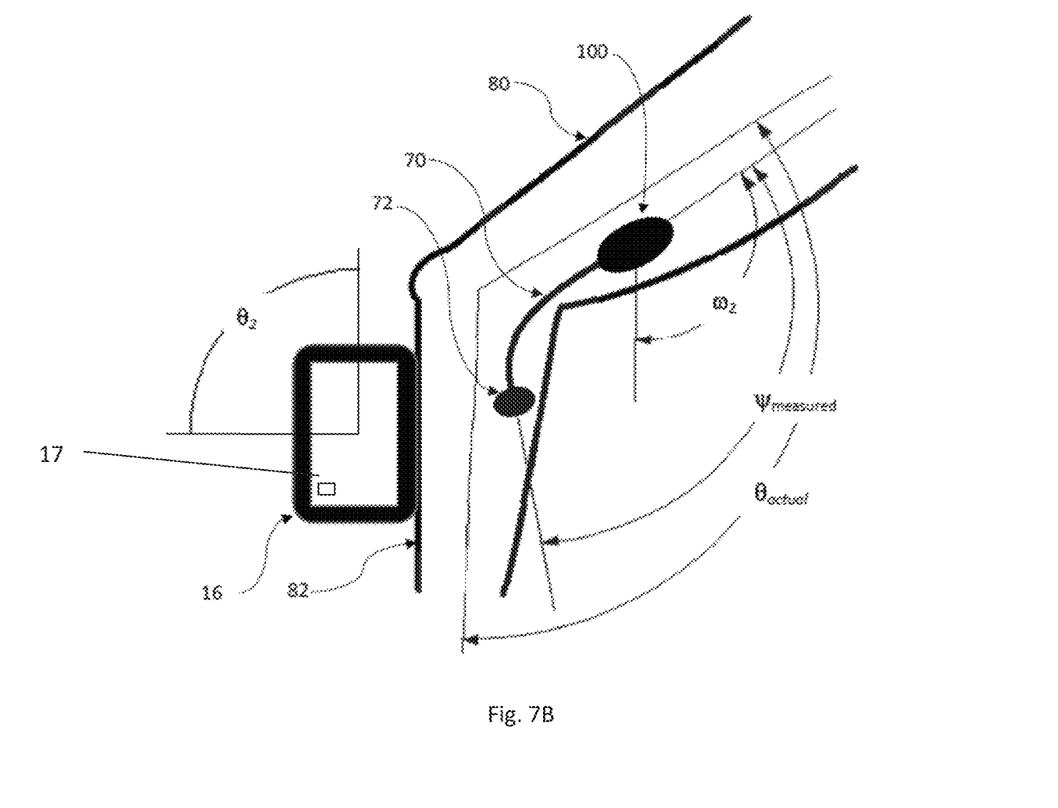
FIG. 7B is an illustration of a calibration procedure that may be followed to calibrate the sensor according to the invention, illustrating a calibration device positioned on the shank of the patients leg.

FIG. 7 illustrates a method for using the apparatus to calibrate the flex sensors, regardless of what orientation they may be applied to the thigh and shank of patient 52. The calibration method uses the three-axis accelerometer 17 defined by software incorporated in local computer 16. In FIG. 7, it can be seen that the actual angle between thigh 80 and shank 82, marked as $\theta_{actual}$, is obviously different from the angle measured between the end points of bend sensor 70, marked as $\psi_{measured}$, due to the end points of bend sensor 70 being attached to thigh 80 and shank 82 in an orientation not in line with the axes of thigh 80 and shank 82.

To begin the calibration, patient 52 sits with their leg in a stable position, with the knee joint flexed to a comfortable degree. Patient 52 then places one edge or face of local computer 16 against and upon the top surface of their thigh 80. In FIG. 7, use of the bottom edge of local computer 16 is illustrated, but the calibration method will work equally well with any of the four edges or front or back faces of local computer 16. Once patient 52 has placed local computer 16 against thigh 80, they touch a control on the touch screen of local computer 16 to simultaneously record two measurements using the software that defines three axis accelerometer 17: a first angle $\theta_1$, which is the current angle of local computer 16 with respect to the direction of gravity as measured by its internal accelerometers; and first angle $\omega_1$ which is the angle of the gravitational vector measured by motion sensor 34, which is inside sensor casing 100. Now patient 52 moves local computer 16 and places it against and upon shank 82, making sure to use the same edge of local computer 16 as used in the previous step as shown on the right in FIG. 7. Once in position, patient 52 touches a control on local computer 16 to simultaneously record three more measurements: a second angle $\theta_2$, which is the new angle of local computer 16 with respect to the direction of gravity as measured by its internal accelerometers; second angle $\omega_2$ which is the angle of the gravitational vector measured by motion sensor 34; and angle $\psi_{measured}$ which is the flexion angle measured by bend sensor 70 when the second measurement is made. (Note that angle $\psi_{measured}$ could equally well be determined using the data from motion sensors 30 and 34 described in the previously described embodiment and applying the Kalman filter algorithm described above to determine the detected flex angle.) From the measurements, software on local computer 16 then calculates a correction factor $\Delta\omega=\omega_1-\omega_2$ is calculated, representing any change in the angle of thigh 80 with respect to the direction of the gravitational vector between the first and the second measurement. Note that sufficient calibration accuracy can be achieved without determining the correction factor in cases where patient 52 is able to maintain the position of their leg between the two measurements.

Using the correction factor, it is now possible to calculate a calibration constant C which represents the difference between the angle $\psi_{measured}$ and the actual flex angle of the knee $\theta_{actual}$, wherein constant $C=(\theta_2-\theta_1-\Delta\omega)-\psi_{measured}$. This calibration constant can now be added to any value of $\psi_{measured}$ to derive $\theta_{actual}$.

Figure 8A:
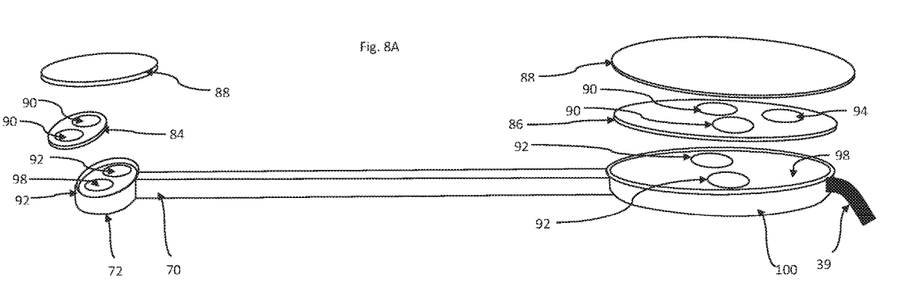
FIG. 8A is an exploded and perspective view illustrating apparatus to allow sensors according to the invention to be removed from and replaced on a patient's limb.
Figure 8B:
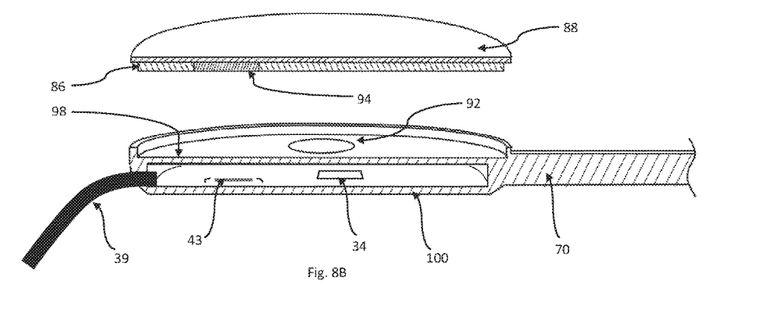
FIG. 8B is a close up and cross sectional view of one end of the apparatus shown in FIG. 8A.

During the course of their recovery, patient 52 may wish to remove the sensor apparatus from their leg to permit bathing or showering, then replace the sensor on their knee. To avoid the need to re-calibrate the sensor each time this is done, it is advantageous to be able to remove and replace the sensor apparatus while maintaining the original position and orientation of the sensor elements. FIG. 8 shows an apparatus that permits easy removal and replacement of the sensor apparatus consisting of sensor casing 100 (which encloses motion sensor 34 and, anchor 72 and bend sensor 70, while maintain the location and position of the elements with respect to the leg of patient 52.

In FIG. 8, anchor 72 and sensor casing 100 are molded shapes that include asymmetrical recessed features 98 that are disposed to engage with molded elements 84 and 86 such that when engaged, elements 84 and 86 are unable to rotate or translate in the plane of anchor 72 or sensor casing 100. Embedded in anchor 72 and sensor casing 100 are magnets 92, which are oriented to attract magnets 90 that are embedded in elements 84 and 86. Element 86 also incorporates magnet 94, which is located so as to be close to magnetic switch 43 when element 86 is fitted into recessed feature 98 on sensor casing 100. Adhesive pads 88 (shown displaced from elements 84 and 86 in the upper FIG. 8A for clarity) are bonded to elements 84 and 86 such that elements 84 and 86, including the incorporated magnets, can be adhered to the leg of patient 52. In use, elements 84 and 86 are attached to the leg of patient 52 using adhesive pads 88. Sensor casing 100 is then located over element 86 such that magnets 90 and 92 attract, pulling casing 100 onto element 86, forcing element 86 to engage into recessed feature 98, thereby ensuring alignment of element 86 and casing 100. When so engaged, magnet 94 is brought into proximity with magnetic switch 43, causing magnetic switch 43 to close, which causes the voltage on input D0 on microprocessor 42 to rise, instructing microprocessor 42 to switch to full power operation. A similar process is followed with anchor 72—element 84 is attached to the leg of patient 52 using adhesive pad 88 which is bonded to element 84, then anchor 72 is brought into proximity of element 84, which causes magnets 90 and 92 to attract, forcing element 84 to fit into recess 98 in anchor 72, thereby aligning element 84 and anchor 72. This arrangement makes it possible for patient 52 to easily remove the sensor elements consisting of sensor case 100, sensor 70 and anchor 72, while leaving elements 86 and 84 attached to their leg, then reattach the sensor elements at a later time while ensuring that they return to their original position and orientation on the leg of patient 52. Advantageously, removing the sensor elements allows magnetic switch 43 to open, causing the voltage on input pin D0 of microprocessor 42, thereby instructing microprocessor 42 to complete any operations then underway, then enter a low power consumption mode, thereby conserving battery power when the sensors are not in use.

Many variations on the preferred embodiment described here can be easily imagined. For example, although the invention as herein described is shown as used for a knee joint, it can easily be extended to operate in a similar fashion for any other joint on which surgery may be performed. The sensors described are one choice of many possibilities for measuring joint motion and temperature, and the choice of a data logger with local memory and periodic uploading could be eliminated in favour of real-time transfer of data from sensors 10 to local computer 16. Furthermore, it is possible to eliminate the cable and I2C bus by having each sensor connected to a separate Bluetooth radio linked to the local computer. It is also clear that there are other mathematical techniques for filtering data from accelerometers and gyroscopes to improve their accuracy and extracting the angle between sensors 30 and 34, many of which could provide equally useful measurements.

While the present invention has been described in terms of preferred and illustrated embodiments, it will be appreciated by those of ordinary skill that the spirit and scope of the invention is not limited to those embodiments, but extend to the various modifications and equivalents as defined in the appended claims.

We claim:

1. A method for calibrating a bend sensor measuring the flexion of a patient's knee, comprising the steps of:
    a. providing a portable computer having an accelerometer capable of measuring the orientation of the computer with respect to a gravitational vector;
    b. attaching a bend sensor between the patient's thigh and shank;
    c. orienting a selected first face or edge of the computer on the patient's thigh and with the computer recording a first angular orientation of the computer with respect to the gravitational vector;
    d. with the bend sensor, recording a first estimated flexion angle between the patient's thigh and the patient's shank at the same time as the first angular orientation is recorded;
    e. orienting the selected first face or edge of the computer on the patient's shank and with the computer recording a second angular orientation of the computer with respect to the gravitational vector; and
    f. calculating the difference between the first and second angular orientations to determine the actual angle of flexion of the patient's knee to thereby calibrate the bend sensor.

2. The method according to claim 1 in which calibrating the bend sensor includes the steps of:
    a. generating a correction factor as the difference between the first estimated flexion angle and the actual angle; and
    b. combining the correction factor with new estimated flexion angles to determine new actual angles.

3. The method according to claim 2 in which the bend sensor further comprises a first accelerometer on the patient's thigh and a second accelerometer on the patient's shank.

4. The method according to claim 3 in which the first estimated angle is determined with the first and second accelerometers.

5. The method according to claim 1 in which step e further comprises orienting another selected edge or face of the computer on the patient's shank.

6. The method of claim 2, including the step of recording, with the bend sensor, a second estimated flexion angle between the patient's thigh and the patient's shank at the same time as the second angular orientation is recorded.

7. The method according to claim 6 including the steps of:
   a. generating a calibration constant C;
   b. adding the calibration constant C to the second estimated flexion angle to derive the actual angle.

8. The method according to claim 7 in which C is calculated according to the following equation:

$$C=(\theta_2-\theta_1-\Delta\omega)-\psi_{measured},$$

in which wherein:
   a. $\theta_2$ is the second angular orientation;
   b. $\theta_1$ is the first angular orientation,
   c. $\Delta\omega$ is the difference between first estimated flexion angle and the second estimated flexion angle; and
   d. $\psi_{measured}$ is the second estimated flexion angle between the patient's thigh and the patient's shank measured at the same time as the second angular orientation $\theta_2$.

9. A method for calibrating a bend sensor measuring the flexion of a patient's knee, comprising the steps of:
   a. providing a portable computer with a computer accelerometer capable of measuring the orientation of the computer with respect to gravity;
   b. attaching a bend sensor between the patient's thigh and shank;
   c. attaching a thigh accelerometer to the patient's thigh capable of measuring the orientation of the patient's thigh with respect to gravity;
   d. positioning the portable computer on the patient's thigh so that a selected edge or face of the portable computer rests on the thigh;
   e. recording a first orientation of the portable computer with respect to gravity with the computer accelerometer, and a first orientation of the patient's thigh with respect to gravity with the thigh accelerometer;
   f. positioning the selected one edge or face of the portable computer on the patient's shank so the selected one edge or face rests on the shank;
   g. recording a second orientation of the portable computer with respect to gravity with the computer accelerometer, and a second orientation of the patient's thigh with respect to gravity with the thigh accelerometer;
   h. with the bend sensor, recording a first estimated flexion angle of the patient's knee between the thigh and shank at the same time as the second orientation of the portable computer and the second orientation of the patient's thigh are recorded; and
   i. calculating the difference between the first orientation of the portable computer and the second orientation of the portable computer and subtracting the difference between the first orientation of the patient's thigh and the second orientation of the patient's thigh to thereby determine a first actual angle of flexion of the patient's knee to thereby calibrate the bend sensor.

10. The method according to claim 9 including the step of establishing a correction factor C, wherein C is determined by the difference between the first estimated flexion angle and the first actual angle of flexion.

11. The method according to claim 10 including the steps of:

a. with the bend sensor, generating a new estimated flexion angle of the patient's knee between the thigh and shank; and
b. adding C to the new estimated flexion angle to thereby determine a new actual angle of flexion.

12. The method according to claim 11 in which C is calculated according to the equation:

$$C=(\theta_2-\theta_1-\Delta\omega)-\psi_{measured},$$

in which:
   a. $\theta_2$ is the second angular orientation of the portable computer;
   b. $\theta_1$ is the first angular orientation of the portable computer,
   c. $\Delta\omega$ is the difference between the first and second recorded orientations of the patient's thigh; and
   d. $\psi_{measured}$ is the first estimated flexion angle measured in step h.

13. The method according to claim 12 in which $\Delta\omega$ is calculated according to the equation:

$$\Delta\omega=\omega_1-\omega_2$$

in which:
   a. $\omega_1$ is the first recorded angle of the thigh relative to the gravitational vector measured by the thigh accelerometer; and
   b. $\omega_2$ is the second recorded angle of the thigh relative to the gravitational vector measured by the thigh accelerometer.

14. A method for calibrating a sensor measuring the flexion of a patient's knee, comprising the steps of:
   a. attaching a first accelerometer to a patient's thigh;
   b. attaching a second accelerometer to a patient's shank;
   c. recording a first orientation of the patient's thigh with respect to gravity with the first accelerometer and recording a first orientation of the patient's shank with respect to gravity with the second accelerometer;
   d. aligning a selected edge or face of a portable computer on the patient's thigh, the portable computer including accelerometers adapted for measuring the orientation of the computer with respect to gravity, and recording a first orientation of the computer;
   e. aligning the selected edge or face of a portable computer on the patient's shank and recording a second orientation of the computer;
   f. recording a second orientation of the patient's thigh as measured by the first accelerometer and the recording a second orientation of the patient's shank as measured by the second accelerometer;
   g. determining the difference between the first orientation of the patient's thigh and the first orientation of the patient's shank to generate a first estimated angle between the patient's thigh and shank;
   h. determining the difference between the second orientation of the patient's thigh and the second orientation of the patient's shank to generate a second estimated angle between the patient's thigh and shank;
   i. calculating the difference between the first orientation of the patient's thigh and the second orientation of the patient's thigh to measure any change in position of the patient's thigh between the first and second orientations of the computer;
   j. calculating the difference between the first estimated angle between the patient's thigh and shank and the second estimated angle between the patient's thigh and shank to measure any change in the flexion angle of the patient's knee between the recording of the first and second orientations of the computer; and k. calculating the difference between the first and second orientations of the computer, subtracting the measured change in the position of the patient's thigh from step l and subtracting the measured change in the flexion angle from step j to determine a first actual angle of flexion of the patient's knee to thereby calibrate the bend sensor.

15. The method according to claim 14 including subtracting the second estimated angle and the first actual angle to establish a correction factor.

\* \* \* \* \*